United States Patent [19]

Bardy

[11] Patent Number: 5,292,338
[45] Date of Patent: Mar. 8, 1994

[54] ATRIAL DEFIBRILLATOR EMPLOYING TRANSVENOUS AND SUBCUTANEOUS ELECTRODES AND METHOD OF USE

[75] Inventor: Gust H. Bardy, Seattle, Wash.
[73] Assignee: Medtronic, Inc., Minneapolis, Minn.
[21] Appl. No.: 922,587
[22] Filed: Jul. 30, 1992
[51] Int. Cl.$^5$ .............................................. A61N 1/36
[52] U.S. Cl. ........................................... 607/5; 607/7
[58] Field of Search ..................................... 128/419 D

[56] References Cited

U.S. PATENT DOCUMENTS

| | | | |
|---|---|---|---|
| Re. 27,652 | 5/1973 | Mirowski | 128/419 D |
| 3,738,370 | 6/1973 | Charms | 128/419 D |
| 3,942,536 | 3/1976 | Mirowski | 128/419 D |
| 3,952,750 | 4/1976 | Mirowski et al. | 128/419 D |
| 4,161,952 | 7/1979 | Kinney et al. | 128/786 |
| 4,375,817 | 3/1983 | Engle et al. | 128/419 D |
| 4,384,585 | 5/1983 | Zipes | 128/419 D |
| 4,481,953 | 11/1984 | Gold et al. | 128/786 |
| 4,577,633 | 3/1986 | Berkvits et al. | 128/419 PG |
| 4,587,970 | 5/1986 | Holley et al. | 128/419 PG |
| 4,726,380 | 2/1988 | Vollmann et al. | 128/419 PG |
| 4,727,380 | 2/1988 | Miura et al. | 346/108 |
| 4,727,877 | 3/1988 | Kallok | 128/419 D |
| 4,800,883 | 1/1989 | Winstrom | 128/419 D |
| 4,830,006 | 5/1989 | Haluska et al. | 128/419 PG |
| 4,880,005 | 11/1989 | Pless et al. | 128/419 PG |
| 4,922,927 | 5/1990 | Fine et al. | 128/786 |
| 4,934,049 | 6/1990 | Kiekhafer et al. | 128/419 P |
| 4,949,719 | 8/1990 | Pless et al. | 128/419 D |
| 4,953,551 | 9/1990 | Mehra et al. | 128/419 D |
| 5,042,143 | 8/1991 | Holleman et al. | 29/875 |
| 5,099,838 | 3/1992 | Bardy | 128/419 D |
| 5,165,403 | 11/1992 | Mehra | 128/419 D |

OTHER PUBLICATIONS

"Onset and Stability For Ventricular Tachyarrhythmia Detection in an Implantable Pacer-Cardioverter-Defibrillator" by Olson et al., published in Computers In Cardiology, Oct. 7-10, 1986, IEEE Computer Society Press, pp. 167-170.

"Elective Countershock in Atrial Fibrillation with an Intracardiac Electrode-A Preliminary Report", by Jain et al., published in the Journal of The Assoc. of Physicians of India, vol. 18, pp. 821-824, 1970.

"Safety and Feasibility of Trasvenous Cardioversion in Atrial Tachycardia" by Blanc et al., published in Cardiac Pacing, edited by Gomez, Futura Publ. Co., 1985, pp. 1526-1529.

Primary Examiner—William E. Kamm
Assistant Examiner—Scott M. Getzow
Attorney, Agent, or Firm—Reed A. Duthler; Harold R. Patton

[57] ABSTRACT

An atrial and ventricular defibrillation pulse generator and lead system particularly adapted to allow for implant via a single incision. The electrode system consists of a right ventricular electrode and a single subcutaneous electrode, which is preferably located on the housing of the implantable defibrillator. The ventricular and subcutaneous electrodes are used for both atrial and ventricular defibrillation, with higher energy pulses being delivered during ventricular defibrillation. The defibrillator is preferably planted in the left pectoral region of the body, and includes a pulse generator for applying biphasic defibrillation pulses between the two electrodes.

16 Claims, 2 Drawing Sheets

FIG. I

ATRIAL DEFIBRILLATOR EMPLOYING TRANSVENOUS AND SUBCUTANEOUS ELECTRODES AND METHOD OF USE

BACKGROUND OF THE INVENTION

The present invention relates to medical electrical leads generally, and more particularly to implantable defibrillation electrodes and leads.

Early concepts of implantable defibrillators, such as disclosed in Reissue U.S. Pat. No. 27,652 by Mirowski, et al, envision an electrode system employing a ventricular endocardial electrode and a plate electrode mounted to the heart directly, subcutaneously, or to the skin. U.S. Pat. No. 3,942,536 by Mirowski, et al, discloses a transvenous lead having electrodes intended for location in the right ventricular apex and in the superior vena cava. This electrode system is disclosed as useful for either ventricular or atrial defibrillation. Such systems were eventually tested in human beings, with some success. Currently available implantable defibrillators typically employ epicardial or subcutaneous patch electrodes, alone, or in conjunction with one or more transvenous electrodes.

It is generally believed that it would be desirable to produce an implantable defibrillation system which entirely avoids the necessity of a thoracotomy, and there has been substantial work directed towards development of multi-electrode systems to accomplish this result, as disclosed in U.S Pat. No. 4,727,877 issued to Kallok, U.S. Pat. No. 4,708,145 issued to Tacker, et al, and as disclosed in U.S. Pat. No. 5,099,838, issued to Bardy. Other endocardial defibrillation electrodes are disclosed in U.S. Pat. No. 4,481,953 issued to Gold et al, U.S. Pat. No. 4,161,952 issued to Kinney, et al, U.S. Pat. No. 4,934,049 issued to Kiekhafer et al and in U.S. Pat. No. 5,042,143 issued to Holleman, et al. The Kinney, Gold, Holleman and Kiekhafer patents all disclose endocardial defibrillation leads employing defibrillation electrodes fabricated from elongated coils of biocompatible metal, mounted exposed to the exterior of the defibrillation lead, for location in the right ventricle and other locations within the heart. The above-cited Smits patent and the Mehra application both disclose a variety of endocardial defibrillation electrodes intended for use in the atrium, ventricle and coronary sinus, all of which employ electrodes taking the form of elongated coils of conductive biocompatible metals.

A return to lead systems employing only two electrodes for ventricular defibrillation is suggested in U.S. Pat. No. 4,922,927, issued to Fine et al. This patent proposes the use of an electrode system as in the above-cited Mirowski reissue Patent, using only a right ventricular electrode and a subcutaneous electrode, which may correspond to prior art subcutaneous electrodes or may be the metal enclosure of the defibrillator. The right ventricular electrode carries an elongated coil electrode fabricated of a copper-zirconium alloy coated with iridium oxide. The use of biphasic pulses in such a two electrode system is also recommended. However, no recommendation is given as to the preferred polarity for the leading phase of the biphasic pulse. The Fine patent states that ventricular defibrillation thresholds as low as 7-10 joules may be achieved with such an endocardial lead in conjunction with a subcutaneous electrode, apparently implanted in proximity to the ventricles, rather than pectorally. There is no suggestion to employ this electrode configuration for ventricular defibrillation.

Concurrent with the development of lead systems adapted to treat ventricular fibrillation, there has also been some work directed to the development of lead systems to treat atrial fibrillation. Synchronized cardioversion using two electrodes located on a lead located in the right atrium is disclosed in U.S. Pat. No. 3,738,370, issued to Charms. A later system is disclosed in U.S. Pat. No. 3,952,750, issued to Mirowski et al, employing one electrode in the atrium and presumably a second electrode at an unspecified location. Neither of these references discloses a specific embodiment for the electrodes located in the atrium.

An electrode lead system specifically designed for atrial defibrillation is disclosed in the article "Elective Countershock in Atrial Fibrillation With an Intracardiac Electrode—A Preliminary Report, by Jain, et al, published in the *Journal of the Association of Physicians of India*, Vol. 18, pp 821-824, 1970. This lead was provided with a 10 mm silver electrode for location in the right atrium and was tested in conjunction with either a second electrode located in the right atrium or a second, cutaneous electrode located on the left side of the chest wall. A second electrode system specifically designed for use in atrial cardioversion is disclosed in the article "Safety and feasibility of transvenous cardioversion in atrial tachycardia", by Blanc et al, published in *Cardiac Pacing*, edited by Gomez, Futura Pub. Co., 1985, pp 1526-1529. This electrode system employed a single lead with electrodes located in the atrium and pulmonary artery. More recently, the use of electrodes located in the right atrium and coronary sinus for atrial defibrillation has been disclosed in allowed U.S. patent application Ser. No. 07/661,568 by Mehra, filed Feb. 26, 1991, incorporated herein by reference in its entirety.

SUMMARY OF THE INVENTION

The present invention is directed toward the provision of a defibrillation lead system particularly optimized for use in defibrillation or cardioversion of the atrium. The lead system includes a right ventricular electrode and a subcutaneous plate electrode located in the left pectoral region, which may optionally take the form of a surface of the defibrillator housing. As discussed in pending U.S. patent application Ser. No. 07/834,446, by Bardy, such an electrode system is particularly beneficial in accomplishing ventricular defibrillation. However, this electrode configuration, developed originally for ventricular defibrillation, surprisingly is optimized to perform atrial defibrillation as well. Thus, the invention may usefully be practiced in a device which is intended to perform atrial cardioversion and defibrillation only, or in a device which also performs ventricular defibrillation. The ability to provide optimal therapy in both the atria and the ventricles using only a single pair of large surface electrodes is a significant benefit provided by the invention.

The present invention is preferably practiced in a defibrillator/cardioverter which delivers an asymmetrical biphasic capacitive discharge pulse between the two electrodes. The initial phase of the pulse is delivered using the subcutaneous electrode as the cathode (coupled to the negatively charged terminal of the output capacitor during the initial phase).

DETAILED DESCRIPTION OF THE PREFERRED EMBODIMENT

Figure 1:
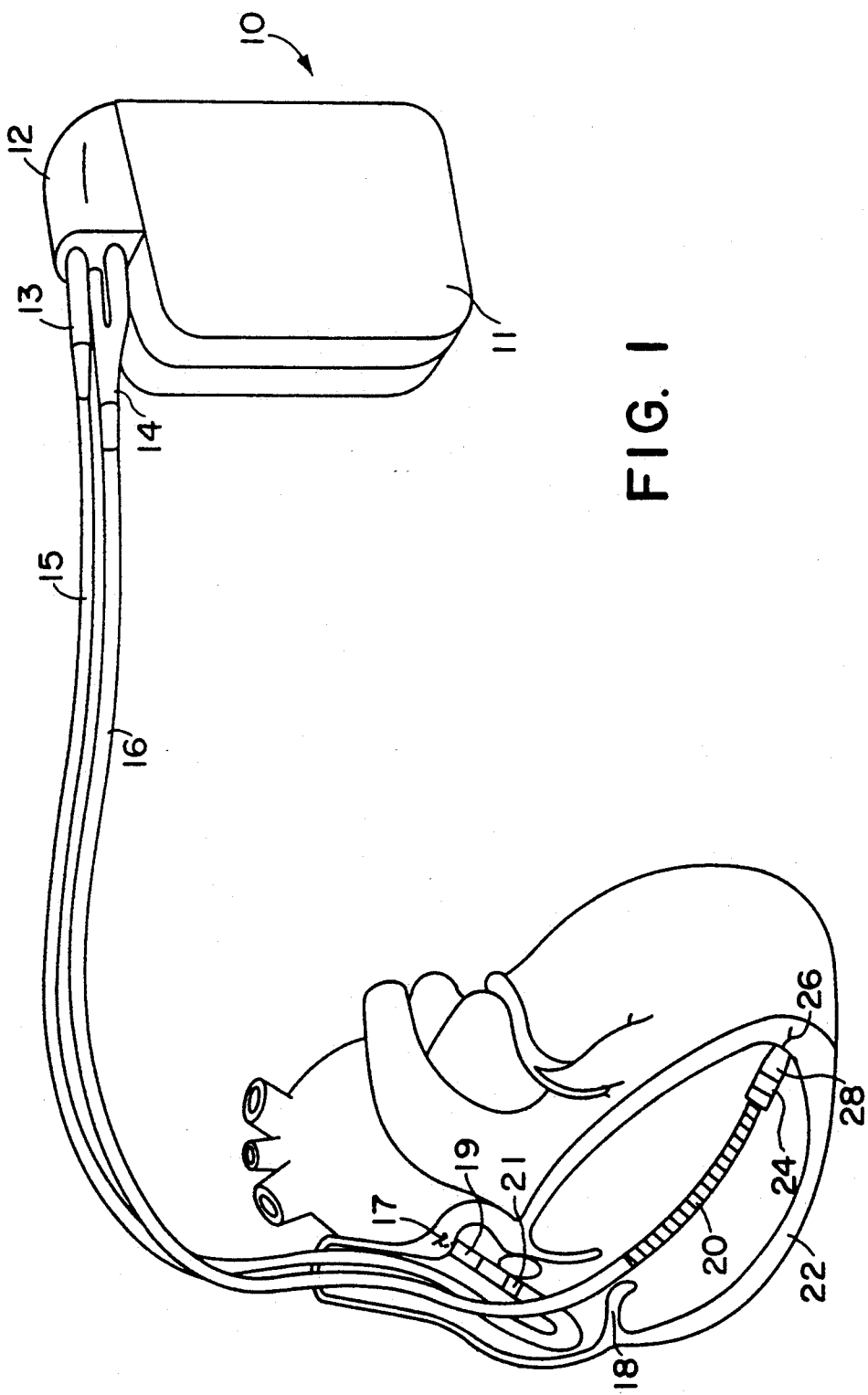
FIG. 1 illustrates the implantable defibrillator and lead according to the present invention.

FIG. 1 illustrates a defibrillator and lead set according to the present invention. The ventricular lead takes the form of the lead disclosed in the above cited patent issued to Bardy, and includes an elongated insulative lead body 16, carrying three concentric coiled conductors, separated from one another by tubular insulative sheaths. Located adjacent the distal end of the lead are a ring electrode 24, an extendable helix electrode 26, mounted retractably within an insulative electrode head 28, and an elongated coil electrode 20. Each of the electrodes is coupled to one of the coiled conductors within the lead body 16. Electrodes 24 and 26 are employed for cardiac pacing and for sensing ventricular depolarizations. At the proximal end of the lead is a bifurcated connector which carries three electrical connectors, each coupled to one of the coiled conductors. The defibrillation electrode 20 may be fabricated from platinum, platinum alloy or other materials known to be usable in implantable defibrillation electrodes.

The atrial lead takes the form of includes an elongated insulative lead body 15, carrying two concentric coiled conductors, separated from one another by tubular insulative sheaths. Located adjacent the J-shaped distal end of the lead are a ring electrode 21 and an extendable helix electrode 17, mounted retractably within an insulative electrode head 19. Each of the electrodes is coupled to one of the coiled conductors within the lead body 16. Electrodes 17 and 21 are employed for atrial pacing and for sensing atrial depolarizations. At the proximal end of the lead is an in-line connector which carries two electrical connectors, each coupled to one of the coiled conductors.

An implantable pacemaker/cardioverter/defibrillator 10 is shown in combination with the leads, with the lead connector assemblies 13 and 14 inserted into the connector block 12. Optionally, insulation of the outward facing portion of the housing 11 of the pacemaker/cardioverter/defibrillator 10 may be provided using a plastic coating, for example parylene or silicone rubber, as is currently employed in some unipolar cardiac pacemakers. However, the outward facing portion may instead be left uninsulated, or some other division between insulated and uninsulated portions may be employed. The uninsulated portion of the housing 11 serves as a subcutaneous defibrillation electrode, used in conjunction with electrode 20 to defibrillate either the atria or ventricles.

The electrode system and method of the present invention has the important advantages of simplicity of construction and of use. Unlike systems involving subcutaneous electrodes located at approximately the level of the heart, the pectoral location of the electrode of the present invention allows for implant using only a single incision. This benefit is accomplished without the necessity of fabrication of defibrillation leads carrying multiple defibrillation electrodes while still retaining the low defibrillation thresholds attributed to the prior art multiple electrode lead systems.

This particular electrode configuration also has advantages in regard to optimizing current distribution with respect to the heart. The right ventricular lead, as a practical matter generally lies along the posterior, inner wall of the right ventricle. The pectoral location of the defibrillator is located anterior to the heart. The bulk of the mass of the atria and ventricles lies between the electrodes. Thus, in this two electrode system, the pectoral site is close to ideal for both atrial and ventricular defibrillation, and eliminates the necessity for separate defibrillation electrode systems for the atria and ventricles.

In acute human clinical testing, the inventor has determined that a defibrillator/lead system according to the present invention provides effective ventricular defibrillation at pulse energies of approximately eight joules. It is believed that atrial defibrillation using this electrode system may be accomplished at a substantially lower energy level. These results for ventricular defibrillation were obtained using a Medtronic right ventricular defibrillation lead, carrying a single platinum coil defibrillation electrode and the inward facing half of the titanium housing of an Medtronic Model 7219 implantable defibrillator. The exterior surface of the half-housing has a surface area of somewhat less than 90 square centimeters, the planar, major surface having an area of approximately 60 square centimeters. As tested, the interior surface of the housing was uninsulated. The half-housing was located in the left infraclavicular pectoral region and was employed as the cathodal electrode during the initial phase of the biphasic defibrillation pulse.

Figure 2:
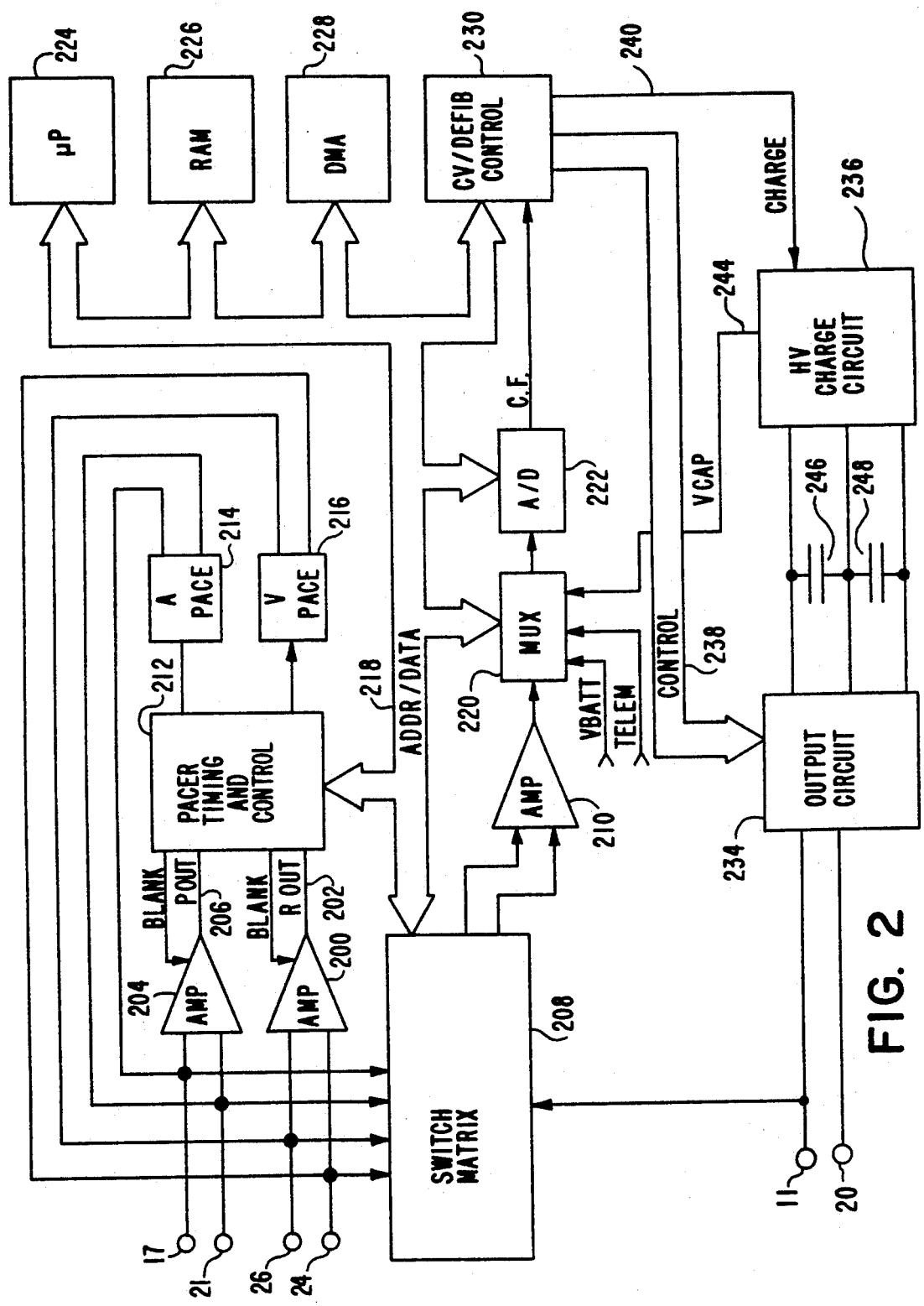
FIG. 2 illustrates a functional schematic diagram of an implantable pacemaker/cardioverter/defibrillator in which the invention may usefully be practiced.

FIG. 2 is a functional schematic diagram of an implantable pacemaker/cardioverter/defibrillator in which the present invention may usefully be practiced. This diagram should be taken as exemplary of the type of device in which the invention may be embodied, and not as limiting, as it is believed that the invention may usefully be practiced in a wide variety of device implementations, including cardioverter and defibrillators which do not provide antitachycardia pacing therapies.

The device is provided with an electrode system including electrodes as illustrated in FIGS. 1. Electrode 11 is the uninsulated portion of the housing of the implantable pacemaker/cardioverter/defibrillator. Electrode 20 is a defibrillation electrode located in the right ventricle and is coupled to high voltage output circuit 234. Electrodes 24 and 26 are located on or in the ventricle and are coupled to the R-wave amplifier 200, which preferably takes the form of an automatic gain controlled amplifier providing an adjustable sensing threshold as a function of the measured R-wave amplitude. A signal is generated on R-out line 202 whenever the signal sensed between electrodes 612 and 614 exceeds the present sensing threshold.

Electrodes 17 and 21 are located on or in the atrium and are coupled to the P-wave amplifier 204, which preferably also takes the form of an automatic gain controlled amplifier providing an adjustable sensing threshold as a function of the measured R-wave amplitude. A signal is generated on P-out line 206 whenever the signal sensed between electrodes 618 and 620 exceeds the present sensing threshold. The general operation of the R-wave and P-wave amplifiers 200 and 204 may correspond to that disclosed in allowed, commonly assigned, copending U.S. patent application Ser. No. 07/612,760, by Keimel, et al., filed November 15, for an Apparatus for Monitoring Electrical Physiologic Signals, incorporated herein by reference in its entirety.

Switch matrix 208 is used to select which of the available electrodes are coupled to wide band (0.5-200 Hz) amplifier 210 for use in digital signal analysis. Selection of electrodes is controlled by the microprocessor 224 via data/address bus 218, which selections may be varied as desired. Signals from the electrodes selected for coupling to bandpass amplifier 210 are provided to multiplexer 220, and thereafter converted to multibit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known in the prior art. An exemplary apparatus is disclosed of accomplishing pacing, cardioversion and defibrillation functions follows. The pacer timing/control circuitry 212 includes programmable digital counters which control the basic time intervals associated with DDD, VVI, DVI, VDD, AAI, DDI and other modes of single and dual chamber pacing well known to the art. Circuitry 212 also controls escape intervals associated with antitachyarrhythmia pacing in both the atrium and the ventricle, employing any antitachyarrhythmia pacing therapies known to the art.

Intervals defined by pacing circuitry 212 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 226, in response to stored data in memory 226 and are communicated to the pacing circuitry 212 via address/data bus 218. Pacer circuitry 212 also determines the amplitude of the cardiac pacing pulses under control of microprocessor 224.

During pacing, the escape interval counters within pacer timing/control circuitry 212 are reset upon sensing of R-waves and P-waves as indicated by a signals on lines 202 and 206, and in accordance with the selected mode of pacing on timeout trigger generation of pacing pulses by pacer output circuitry 214 and 216, which are coupled to electrodes 118, 120, 112, 114. The escape interval counters are also reset on generation of pacing pulses, and thereby control the basic timing of cardiac pacing functions, including anti-tachy pacing. The durations of the intervals defined by the escape interval timers are determined by microprocessor 224, via data/address bus 218. The value of the count present in the escape interval counters when reset by sensed R-waves and P-waves may be used to measure the durations of R-R intervals, P-P intervals, P-R intervals and R-P intervals, which measurements are stored in memory 226 and used to detect the presence of tachyarrhythmias.

Microprocessor 224 operates as an interrupt driven device, and is awakened by interrupts from pacer timing/control circuitry 212 corresponding to the occurrence sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts.

For example, in response to a sensed or paced ventricular depolarization or R-wave, the intervals separating that R-wave from the immediately preceding R-wave, paced or sensed (R-R interval) and the interval separating the paced or sensed R-wave from the preceding atrial depolarization, paced or sensed (P-R interval) may be stored. Similarly, in response to the occurrence of a sensed or paced atrial depolarization (P-wave), the intervals separating the sensed P-wave from the immediately preceding paced of sensed atrial contraction (P-P Interval) and the interval separating the sensed P-wave from the immediately preceding sensed or paced ventricular depolarization (R-P interval) may be stored. Preferably, a portion of the memory 226 (FIG. 4) is configured as a plurality of recirculating buffers, capable of holding a preceding series of measured intervals, which may be analyzed in response to the occurrence of a pace or sense interrupt to determine whether the patient's heart is presently exhibiting atrial or ventricular tachyarrhythmia.

Detection of atrial or ventricular tachyarrhythmias, as employed in the present invention, may correspond to tachyarrhythmia detection algorithms known to the art. For example, presence of atrial or ventricular tachyarrhythmia may be confirmed by means of detection of a sustained series of short R-R or P-P intervals of an average rate indicative of tachyarrhythmia or an unbroken series of short R-R or P-P intervals. The suddenness of onset of the detected high rates, the stability of the high rates, or a number of other factors known to the art may also be measured at this time. Appropriate detection methodologies measuring such factors are described in U.S. Pat. No. 4,726,380, issued to Vollmann, U.S. Pat. No. 4,880,005, issued to Pless et al and U.S. Pat. No. 4,830,006, issued to Haluska et al. An additional set of tachycardia recognition methodologies is disclosed in the article "Onset and Stability for Ventricular Tachyarrhythmia Detection in an Implantable Pacer-Cardioverter-Defibrillator" by Olson et al., published in *Computers in Cardiology*, Oct. 7-10, 1986, IEEE Computer Society Press, pages 167-170. However, one of the advantages of the present invention is that it is believed practicable in conjunction with most prior art tachycardia detection algorithms.

In the event that an atrial or ventricular tachyarrhythmia is detected, and an antitachyarrhythmia pacing regimen is desired, appropriate timing intervals for controlling generation of antitachy pacing therapies are loaded from microprocessor 224 into the pacer timing and control circuitry 212, to control the operation of the escape interval counters therein and to define refractory periods during which detection of R-waves and P-waves is ineffective to restart the escape interval counters.

Alternatively, circuitry for controlling the timing and generation of antitachycardia pacing pulses as described in U.S. Pat. No. 4,577,633, issued to Berkovits et al on Mar. 25, 1986, U.S. Pat. No. 4,880,005, issued to Pless et al on Nov. 14, 1989, U.S. Pat. No. 7,726,380, issued to Vollmann et al on Feb. 23, 1988 and U.S. Pat. No. 4,587,970, issued to Holley et al on May 13, 1986, all of which are incorporated herein by reference in their entireties may also be used.

In the event that generation of a cardioversion or defibrillation pulse is required, microprocessor 224 employs the an escape interval counter to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246, 248, 250 and 252 via charging circuit 236, under control of high voltage charging control lines 240 and 242. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212. Following delivery of the fibrillation or tachycardia therapy the microprocessor then returns the device to pacing and awaits the next successive interrupt due to pacing or the occurrence of a sensed atrial or ventricular depolarization.

One embodiment of an appropriate system for delivery and synchronization of cardioversion and defibrillation pulses and for controlling the timing functions related to them is disclosed in more detail in copending, commonly assigned U.S. patent application Ser. No. 07/612,761, by Keimel, for an Apparatus for Detecting and Treating a Tachyarrhythmia, filed Nov. 15, 1990 and incorporated herein by reference in its entirety. However, any known cardioversion or defibrillation pulse generation circuitry is believed usable in conjunction with the present invention. For example, circuitry controlling the timing and generation of cardioversion and defibrillation pulses as disclosed in U.S. Pat. No. 4,384,585, issued to Zipes on May 24, 1983, in U.S. Pat. No. 4,949,719 issued to Pless et al, cited above, and in U.S. Pat. No. 4,375,817, issued to Engle et al, all incorporated herein by reference in their entireties may also be employed.

In the illustrated device, delivery of the cardioversion or defibrillation pulses is accomplished by output circuit 234, under control of control circuitry 230 via control bus 238. Output circuit 234 determines whether a monophasic or biphasic pulse is delivered and whether the housing 11 serves as cathode or anode. An example of output circuitry for delivery of biphasic pulse regimens may be found in the above cited patent issued to Mehra and in U.S. Pat. No. 4,727,877, incorporated by reference in its entirety. Atrial and ventricular defibrillation will be accomplished using the same electrode set (11 and 20), but atrial defibrillation may be accomplished using lower pulse energy levels than required for ventricular defibrillation.

Another example of circuitry which may be used to control delivery of monophasic pulses is set forth in commonly assigned copending patent application Ser. No. 07/612,758, filed by Keimel, for an Apparatus for Delivering Single and Multiple Cardioversion and Defibrillation Pulses, filed Nov. 14, 1990, also incorporated herein by reference in its entirety. However, output control circuitry as disclosed in U.S. Pat. No. 4,953,551, issued to Mehra et al on Sep. 4, 1990 or U.S. Pat. No. 4,800,883, issued to Winstrom on Jan. 31, 1989 both incorporated herein by reference in their entireties, may also be used in conjunction with a device embodying the present invention for delivery of biphasic pulses.

In modern implantable cardioverter/defibrillators, the particular therapies are programmed into the device ahead of time by the physician, and a menu of therapies is typically provided. For example, on initial detection of an atrial or ventricular tachycardia, an antitachycardia pacing therapy may be selected and delivered to the chamber in which the tachycardia is diagnosed or to both chambers. On redetection of tachycardia, a more aggressive antitachy pacing therapy may abe scheduled. If repeated attempts at antitachy pacing therapies fail, a higher level cardioversion pulse may be selected thereafter. Therapies for tachycardia termination may also vary with the rate of the detected tachycardia, with the therapies increasing in aggressiveness as the rate of the detected tachycardia increases. For example, fewer attempts at antitachy pacing may be undertaken prior to delivery of cardioversion pulses if the rate of the detected tachycardia is above a preset threshold. The references cited above in conjunction with descriptions of prior art tachycardia detection and treatment therapies are applicable here as well.

In the event that atrial or ventricular fibrillation is identified, the typical therapy will be delivery of a high amplitude defibrillation pulse, typically in excess of 10 joules in the case of ventricular fibrillation and in excess of 5 joules in the case of atrial defibrillation. Lower energy levels will be employed for cardioversion. As in the case of currently available implantable pacemakers/cardioverter/defibrillators, and as discussed in the above-cited references, it is envisioned that the amplitude of the defibrillation pulse may be incremented in response to failure of an initial pulse or pulses to terminate fibrillation. Prior art patents illustrating such preset therapy menus of antitachyarrhythmia therapies include the above-cited U.S. Pat. No. 4,830,006, issued to Haluska, et al, U.S. Pat. No. 4,727,380, issued to Vollmann et al and U.S. Pat. No. 4,587,970, issued to Holley et al.

While the invention is disclosed above embodied in a dual chamber pacemaker/cardioverter/defibrillator, the invention may also be usefully practiced in substantially simpler devices. For example, the electrode system illustrated in FIG. 1 may simply be coupled to an implantable atrial cardioverter as disclosed in U.S. Pat. No. 3,738,370, issued to Charms, incorporated herein by reference in its entirety. A simple device of this type is believed workable in some patients. However, inclusion of the ability to detect and terminate ventricular tachycardias and fibrillation is believed of extreme importance in patients in whom delivery of atrial cardioversion or defibrillation pulses unintentionally in initiates ventricular arrhythmias.

There are major efforts presently underway to reduce the size of current implantable defibrillators to further simplify implant and enhance patient comfort. As the devices become smaller, it is anticipated that the surface areas of the defibrillator housings may become small enough to interfere ability of the housing to function efficiently as a subcutaneous defibrillation electrode. In such cases, it is envisioned that the surface area of the subcutaneous electrode may be increased by means of a supplemental plate electrode electrically coupled to the defibrillator housing or employed as an electrode in place of the defibrillator housing. This supplemental electrode may be simply placed in the pectoral implant site adjacent the defibrillator or may in some cases be clipped or otherwise attached to the inward facing surface of the defibrillator housing.

In conjunction with the above specification, I claim:

1. An apparatus for defibrillating the atrium of a patient's heart, comprising:
   a first defibrillation electrode means for location in the right ventricle of said patient's heart;
   an implantable defibrillation pulse generator having a housing and having a first output coupled to said first defibrillation electrode; and
   a second defibrillation electrode comprising a conductive portion of said housing of said defibrillation pulse generator and coupled to a second output of said defibrillation pulse generator; and
   means for sensing the occurrence of atrial fibrillation and for triggering the delivery of a defibrillation pulse between said first and second electrodes in response to sensing the occurrence of atrial fibrillation.

2. An apparatus for defibrillating the atrium of a patient's heart, comprising:
   a first defibrillation electrode means for location in the right ventricle of said patient's heart;
   a second defibrillation electrode means for subcutaneous location in the left pectoral region of said patient's thorax;
   an implantable defibrillation pulse generator coupled to said first and second defibrillation electrodes; and
   means for sensing the occurrence of atrial fibrillation and for triggering the delivery of a defibrillation pulse between said first and second defibrillation electrodes in response to sensing the occurrence of atrial fibrillation.

3. An apparatus for defibrillating the atrium and ventricle of a patient's heart, comprising:
   a first defibrillation electrode means for location in the right ventricle of said patient's heart;
   an implantable defibrillation pulse generator having a housing and having a first output coupled to said first defibrillation electrode; and
   a second defibrillation electrode comprising a conductive portion of said housing of said defibrillation pulse generator and coupled to a second output of said defibrillation pulse generator;
   means for sensing the occurrence of atrial fibrillation and for triggering the delivery of a defibrillation pulse at a first energy level between said first and second electrodes in response to sensing the occurrence of atrial fibrillation; and
   means for sensing the occurrence of ventricular fibrillation and for triggering the delivery of a defibrillation pulse at a second, higher energy level between said first and second electrodes in response to sensing the occurrence of ventricular fibrillation.

4. A apparatus according to claim 1 or claim 3 wherein said conductive portion of said housing of said defibrillation pulse generator comprises less than all of said housing.

5. An apparatus for defibrillating the atrium and ventricle of a patient's heart, comprising:
   a first defibrillation electrode means for location in the right ventricle of said patient's heart;
   a second defibrillation electrode means for subcutaneous location in the left pectoral region of said patient's thorax;
   an implantable defibrillation pulse generator coupled to said first and second defibrillation electrodes;
   means for sensing the occurrence of atrial fibrillation and for triggering the delivery of a defibrillation pulse at a first energy level between said first and second defibrillation electrodes in response to sensing the occurrence of atrial fibrillation; and
   means for sensing the occurrence of ventricular fibrillation and for triggering the delivery of a defibrillation pulse at a second, higher energy level between said first and second defibrillation electrodes in response to sensing the occurrence of ventricular fibrillation.

6. An apparatus for defibrillating the atrium and ventricle of a patient's heart, comprising:
   a first defibrillation electrode means for location adjacent the ventricle of said patient's heart;
   a second defibrillation electrode;
   an implantable defibrillation pulse generator coupled to said first and second defibrillation electrodes;
   means for sensing the occurrence of atrial fibrillation and for triggering the delivery of a defibrillation pulse at a first energy level between said first and second defibrillation electrodes in response to sensing the occurrence of atrial fibrillation; and
   means for sensing the occurrence of ventricular fibrillation and for triggering the delivery of a defibrillation pulse at a second, higher energy level between said first and second defibrillation electrodes in response to sensing the occurrence of ventricular fibrillation.

7. An apparatus according to claim 1 or claim 2 or claim 3 or claim 5 or claim 6 wherein said pulse generator comprises means for generating asymmetric biphasic pulses having a first phase and a second phase wherein said first phase of said biphasic pulse has greater amplitude than said second phase of said second biphasic pulse.

8. An apparatus according to claim 7 wherein said pulse generator comprises means for generating asymmetric biphasic pulses such that said second defibrillation electrode serves as the cathodal electrode during said first phase of said biphasic pulse.

9. A method of defibrillating the atrium of a patient's heart, comprising:
   implanting a first transvenous defibrillation electrode in the right ventricle of said patient's heart;
   subcutaneously implanting a defibrillation pulse generator, having a housing including a conductive portion and employing said conductive portion of said housing as a second, subcutaneous defibrillation electrode, in the left pectoral region of said patient's body;
   detecting the occurrence of atrial fibrillation; and
   delivering a defibrillation pulse only between said first, transvenous defibrillation electrode and said portion of said housing of said defibrillation pulse generator.

10. A method of defibrillating the atrium of a patient's heart, comprising:
   implanting a first, transvenous defibrillation electrode in the right ventricle of said patient's heart;
   subcutaneously implanting a defibrillation pulse generator, in said patient's body and a second, subcutaneous defibrillation electrode, in the left pectoral region of said patient's body;
   detecting the occurrence of atrial fibrillation; and
   delivering a defibrillation pulse only between said first, transvenous defibrillation electrode and said second, subcutaneous defibrillation electrode.

11. A method of defibrillating the atrium and ventricle of a patient's heart, comprising:
implanting a first transvenous defibrillation electrode in the right ventricle of said patient's heart;
subcutaneously implanting a defibrillation pulse generator, having a housing including a conductive portion and employing said conductive portion of said housing as a second, subcutaneous defibrillation electrode, in the left pectoral region of said patient's body;
detecting the occurrence of atrial or ventricular fibrillation; and
delivering a defibrillation pulse between said first, transvenous defibrillation electrode and said portion of said housing of said defibrillation pulse generator following detection of atrial or ventricular fibrillation such that following detection of atrial fibrillation a pulse of a first energy level is delivered and such that following detection of ventricular fibrillation a pulse of a second, higher energy level is delivered.

12. A method according to claim 9 or claim 11 wherein said step of subcutaneously implanting a defibrillation pulse generator comprises implanting a generator having a conductive portion which is less than all of said housing.

13. A method of defibrillating the atrium and ventricle of a patient's heart, comprising:
implanting a first, transvenous defibrillation electrode in the right ventricle of said patient's heart;
subcutaneously implanting a defibrillation pulse generator, in said patient's body and a second, subcutaneous defibrillation electrode, in the left pectoral region of said patient's body;
detecting the occurrence of atrial or ventricular fibrillation; and
delivering a defibrillation pulse only between said first, transvenous defibrillation electrode and said second, subcutaneous defibrillation electrode following detection of atrial or ventricular fibrillation such that following detection of atrial fibrillation a pulse of a first energy level is delivered and such that following detection of ventricular fibrillation a pulse of a second, higher energy level is delivered.

14. A method of defibrillating the atrium and ventricle of a patient's heart, comprising:
implanting a first defibrillation electrode adjacent the ventricle of said patient's heart; implanting a second defibrillation electrode;
detecting the occurrence of atrial or ventricular fibrillation; and
delivering a defibrillation pulse between said first and second defibrillation electrodes following detection of atrial or ventricular fibrillation such that following detection of atrial fibrillation a pulse of a first energy level is delivered and such that following detection of ventricular fibrillation a pulse of a second, higher energy level is delivered.

15. A method according to claim 9 or claim 10 or claim 11 or to claim 13 or claim 14 wherein said step of applying a defibrillation pulse comprises applying an asymmetric biphasic pulse wherein the first phase of said biphasic pulse has a higher amplitude than the second phase of said biphasic pulse.

16. A method according to claim 15 wherein said step of applying a defibrillation pulse comprises applying an asymmetric biphasic pulse such that said second, subcutaneous defibrillation electrode serves as the cathodal electrode during the first phase of said biphasic pulse.

* * * * *